US006849266B2

(12) United States Patent
Maupin et al.

(10) Patent No.: US 6,849,266 B2
(45) Date of Patent: Feb. 1, 2005

(54) CONTROL OF ARTHROPOD VECTORS OF PARASITIC DISEASES

(75) Inventors: Gary O. Maupin, Fort Collins, CO (US); Marc C. Dolan, Fort Collins, CO (US)

(73) Assignee: Centers for Disease Control & Prevention, Atlanta, GA (US)

(*) Notice: Subject to any disclaimer, the term of this patent is extended or adjusted under 35 U.S.C. 154(b) by 41 days.

(21) Appl. No.: 10/282,539

(22) Filed: Oct. 28, 2002

(65) Prior Publication Data

US 2003/0087800 A1 May 8, 2003

Related U.S. Application Data

(63) Continuation of application No. 09/595,035, filed on Jun. 16, 2000, now abandoned.

(51) Int. Cl.⁷ .......................... A01N 25/32; A01N 43/56
(52) U.S. Cl. ........................... 424/406; 43/131; 43/136; 119/657; 119/663; 424/409; 424/410; 424/411; 424/84; 514/407
(58) Field of Search ................................ 424/409, 406, 424/84, 410, 411; 514/407; 43/131, 136; 119/339, 532, 535, 656, 657, 663, 664

(56) References Cited

U.S. PATENT DOCUMENTS

| 416,951 A | 12/1889 | Roop ........................ 119/673 |
| 1,569,904 A | 1/1926 | Wright ...................... 119/652 |
| 1,582,144 A | 4/1926 | Pflaum ...................... 119/652 |
| 2,316,932 A | 4/1943 | Bruce ........................ 119/159 |
| 2,925,065 A | 2/1960 | Worden ...................... 119/157 |
| 3,902,461 A | 9/1975 | Cortner ...................... 119/159 |
| 4,074,659 A | 2/1978 | Mowbray et al. ........... 119/159 |
| 4,281,471 A | * 8/1981 | Jenkins et al. ................ 43/131 |
| 4,324,202 A | 4/1982 | Stonestreet et al. ........... 119/51 |
| 4,662,104 A | * 5/1987 | Mather et al. ............. 43/132.1 |
| 4,753,032 A | * 6/1988 | Sherman ...................... 43/131 |
| 5,027,747 A | 7/1991 | Talley ........................ 119/157 |
| 5,232,940 A | 8/1993 | Hatton et al. ............... 514/407 |
| 5,272,832 A | 12/1993 | Marshall et al. ............. 43/131 |
| 5,367,983 A | * 11/1994 | Pound et al. ................ 119/53 |
| 5,447,122 A | 9/1995 | Cortner ...................... 119/159 |
| 5,448,852 A | 9/1995 | Spragins et al. ............. 43/131 |
| 5,806,237 A | 9/1998 | Nelson et al. ................ 43/131 |
| 5,932,437 A | * 8/1999 | Poche ......................... 435/32 |
| 5,983,558 A | * 11/1999 | Las et al. .................... 43/131 |
| 6,162,820 A | * 12/2000 | Jeannin et al. ............. 514/407 |
| 6,395,765 B1 | * 5/2002 | Etchegaray ................. 514/407 |

FOREIGN PATENT DOCUMENTS

| EP | 0 295 117 | * 12/1988 |
| WO | WO 97/12521 | * 4/1997 |
| WO | 98/02042 | * 1/1998 |
| WO | WO 98/42191 | * 10/1998 |

OTHER PUBLICATIONS

Cooper et al. Use of Fipronil—Vet. Record Jul. 27/1996.*
Meo et al. A Comparison of Flea Control Efficacy—Proc. Am. Assoc. Vet. Parasitol. 41 meet 52 1996.*

(List continued on next page.)

Primary Examiner—Neil S. Levy
(74) Attorney, Agent, or Firm—Connolly Bove Lodge & Hutz LLP (57) ABSTRACT

The present invention provides a method for controlling ectoparasites of small rodents, thereby preventing the transmission of diseases by arthropod vectors. The invention further provides an enclosure having openings for entry of rodents, and having arranged therein one or more applicators which are configured to contact rodents entering the chamber and having an ectoparasiticide on the applicator for application to the rodents.

31 Claims, 10 Drawing Sheets

OTHER PUBLICATIONS

Copies of Slides presented at oral presentations by inventors or their assistants prior to Jun. 16, 1999.

Cover page and pp. 1, 5 and 16 of booklet prepared by American Lyme Disease Foundation, Inc. including abstract of presentation given by inventor Gary O. Maupin on Mar. 8, 1999 (date of booklet unknown).

Gate et al., Flea (Siphonaptera: Ceratophyllidae, Hystrichopsyllidae) and Tick (Acarina:Ixodidae) Control on Wood Rats Using Host–Targeted Liquid Permethrin in Bait Tubes; J. Med. Entomol., pp. 46–51, vol. 34, No. 1, (Jan. 1997).

Lane et al., Modified bait tube controls disease–carrying ticks and fleas; California Agriculture; vol. 52, No. 2, cover page and pp. 3, 43–48 (Mar.–Apr. 1998).

Barnes; Surveillance and Control of Bubonic Plague in the United States; Symp. Zool. Soc. Lond., No. 50, 237–270 (1982).

Kartman; An Insecticide–Bait Box Method for Plague Control in Certain Areas of the Pacific Region; Proceedings of the Ninth Pacific Science Congress, vol. 19, pp. 49–52 (1957).

Sonenshine and Haines, A Convenient Method for Controlling Populations of the American Dog Tick, *Dermacentor variabilis* (Acarl:Ixodidae), In the Natural Environment, J. Med. Entomol., vol. 22, No. 5, pp 577–583 (Sep. 1985).

Kartman; Further Observations on an Insecticide–bait–box Method for the Control of Sylvatic Plague Vectors; Effect of Prolonged Field Exposure to DDT Powder; J. Hyg., Camb., vol. 58, pp. 119–124 (1960).

Kartman; An Insecticide–Bait–Box Method for the Control of Sylvatic Plague Vectors; J. Hyg., vol. LVI, pp. 455–465 (1958).

Barnes and Kartman; Control of Plague Vectors on Diurnal Rodents in the Sierra Nevada of California by Use of Insecticide Bait–Boxes; J. Hyg., Camb., vol. 58, pp. 347–355 (1960).

Morris, K. D., Proctor, R.D. and Kaukeinen, D.E., "Design and Evaluation Criteria for Development of Toxic Wicks for Rodent Control," *Vertebrate Pest Control and Management Materials: Fourth Symposium. ASTM STP 817*, D.E. Kaukeinen, Ed., American Society for Testing and Materials, Philadelphia, 1983, pp. 165–182.

Maupin et al., "Laboratory and Field Evaluation of Rodent-–targeted Acaricides for Controlling *Ixodes* ssp", poster presentation of VII International Conference on Lyme Borreliosis and Other Emerging Tick–Borne Diseases, Munich, Germany, presented Jun. 22, 1999.

J.S. Hunter et al.; "A comparison of the tick efficacy of Frontline Spray Treatment against the American Dig Tick and Brown Dog Tick"; Abstract ;Proc. Am. Assoc. Vet. Parasitol. (41 Meet., 51, 1996).*

U.S. Appl. Ser. No. 09/595,177, filed Jun. 16, 2000, Maupin, et al., "Control of Arthropods in Rodents,".*

U.S. Appl. Ser. No. 09/595,034, filed Jun. 16, 2000, Maupin, et al., "Apparatus for Applying Chemicals to Rodents,".*

* cited by examiner

CONTROL OF ARTHROPOD VECTORS OF PARASITIC DISEASES

CROSS-REFERENCE TO RELATED APPLICATION

The present application is a continuation of U.S. patent application Ser. No. 09/595,035 which was filed on Jun. 16, 2000, and is now abandoned, in the names of Gary O. Maupin and Marc C. Dolan.

FIELD OF THE INVENTION

The present invention relates to a method of controlling ectoparasitic vectors of diseases, particularly bacterial or viral diseases.

BACKGROUND OF THE INVENTION

Lyme disease was first recognized in the United States in 1975, after a mysterious outbreak of arthritis near Lyme, Conn. Since then, reports of Lyme disease have increased dramatically, and the disease has become an important public health problem in some areas of the United States. Lyme disease is an infection caused by *Borrelia burgdorferi*, a member of the family of spirochetes, or corkscrew-shaped bacteria.

Lyme disease is spread by the bite of ticks of the genus Ixodes that are infected with *Borrelia burgdorferi*. The deer (or bear) tick, *Ixodes scapularis*, which normally feeds on the white-footed mouse, the white-tailed deer, other mammals, and birds, is responsible for transmitting Lyme disease bacteria to humans in the northeastern and north-central United States. In these regions, this tick is also responsible for the spreading of babesiosis, a disease caused by a malaria-like parasite. On the Pacific Coast, the bacteria are transmitted to humans by the western black-legged tick, *I. pacificus*. Another newly recognized and serious disease that is transmitted by both *I. scapularis* and *I. pacificus* is human granulocytic ehrlichiosis, the pathogen of which is a rickettsial bacterium.

Ixodes ticks are much smaller than common dog and cattle ticks. In their larval and nymphal stages, they are no bigger than a pinhead. Adult ticks are slightly larger. Ticks can attach to any part of the human body but often attach to the more hidden and hairy areas such as the groin, armpits, and scalp. Research in the eastern United States has indicated that, for the most part, ticks transmit Lyme disease to humans during the nymphal stage, probably because nymphs are more likely to feed on a person and are rarely noticed because of their small size (less than two mm). Thus, the nymphs typically have ample time to feed and transmit the infection since ticks are most likely to transmit infection after approximately two or more days of feeding.

Tick larvae are smaller than the nymphs, but they rarely carry the infection at the time of feeding and are probably not important in the transmission of Lyme disease to humans.

Adult ticks can transmit the disease, but since they are larger and more likely to be removed from a person's body within a few hours, they are less likely than the nymphs to have sufficient time to transmit the infection. Moreover, adult Ixodes ticks are most active during the cooler months of the year, when outdoor activity is limited. Adults quest for hosts on grasses, shrubs and brush at heights of up to one meter. Immature Ixodes search for host animals from the tips of grasses and shrubs (not from trees) and leaf litter near the ground and transfer to animals or persons that brush against these substrates. Ticks only crawl; they do not fly or jump. Ticks found on the scalp usually have crawled there from lower parts of the body. Ticks feed on blood by inserting their mouth parts (not their whole bodies) into the skin of a host animal. They are slow feeders: a complete blood meal can take several days. As they feed, their bodies slowly enlarge.

Although in theory Lyme disease could spread through blood transfusions or other contact with infected blood or urine, no such transmission has been documented. There is no evidence that a person can get Lyme disease from the air, food or water, from sexual contact, or directly from wild or domestic animals. There is no convincing evidence that Lyme disease can be transmitted by insects such as mosquitoes, flies, or fleas. Campers, hikers, outdoor workers, and others who frequent wooded, brushy, and grassy places are commonly exposed to ticks, and this may be important in the transmission of Lyme disease in some areas. Because new homes are often built in wooded areas, transmission of Lyme disease near homes has become an important problem in some areas of the United States. The risk of exposure to ticks is greatest in the woods and garden fringe areas of properties, but ticks may also be carried by animals into lawns and gardens.

Geographic distribution of Lyme disease is wide in northern temperate regions of the world. In the United States, the highest incidence occurs in the Northeast, from Massachusetts to Maryland. Incidence is also notable in the North-central states, especially Wisconsin and Minnesota, and the West Coast, particularly northern California. For Lyme disease to exist in an area, at least three closely interrelated elements must be present in nature: the Lyme disease bacteria, ticks that can transmit them, and mammals (such as mice and deer) to provide food for the ticks in their various life stages. Ticks that transmit Lyme disease can be found in temperate regions that may have periods of very low or high temperature and a constant high relative humidity at ground level. Knowing the complex life cycle of the ticks that transmit Lyme disease is important in understanding the risk of acquiring the disease and in finding ways to prevent it: The life cycle of these ticks requires two years to complete. Adult ticks feed and mate on large animals, especially deer, in the fall and early spring. Female ticks then drop off these animals to lay eggs on the ground. By summer, eggs hatch into larvae. Larvae feed on mice and other small mammals and birds in the summer and early fall and then are inactive until the next spring when they molt into nymphs. Nymphs feed on small rodents and other small mammals and birds in the late spring and summer and molt into adults in the fall, completing the 2-year life cycle. Larvae and nymphs typically become infected with Lyme disease bacteria when they feed on infected small animals, particularly the white-footed mouse. The bacteria remain in the tick as it changes from larva to nymph or from nymph to adult. Infected nymphs and adult ticks then bite and transmit Lyme disease bacteria to other small rodents, other animals, and humans, all in the course of their normal feeding behavior. Lyme disease in domestic animals Domestic animals may become infected with Lyme disease bacteria and some of these (dogs, for instance) may develop arthritis. Domestic animals can carry infected ticks into areas where humans live, but whether pet owners are more likely than others to get Lyme disease is unknown.

There are proposed solutions to the prevention of transmission of tick-borne parasites to humans. For example, U.S. Pat. Nos. 5,648,398, 5,346,922, and 5,227,406 describe insect repellent compositions which are claimed to repel ticks. However, the use a repellent does not eliminate the vector itself but serves as a "chemical shield" against the ticks so that they will have to find another mammalian host. There are generally no known solutions to arrest the spread of Lyme disease and/or other diseases spread by ticks.

SUMMARY OF THE INVENTION

An object of the present invention is to provide a method of controlling ticks in non-domestic mammals.

Another object of present invention is to provide a method of preventing the transmission of diseases by arthropod vectors.

These and other objects are met in whole or in part by the present invention.

DETAILED DESCRIPTION OF THE INVENTION

The present invention provides a method of controlling ectoparasites of small rodents comprising providing one or more enclosures of appropriate size to such rodents, the enclosures having one or more peripheral openings allowing entry and egress of rodents, the enclosure including at least one applicator arranged to contact a rodent; providing a composition comprising an ectoparasiticide on the applicator; and placing one or more enclosures in a locus where the rodents are expected, wherein the applicator is arranged and the composition is provided to apply an effective amount of the composition to the skin or hair of the rodent upon contact with the applicator.

The method of the present invention is useful for the control of arthropods that are vectors of diseases such as Lyme disease, Rocky Mountain Spotted Fever, Ehrlichiosis or Babesiosis. In particular, the present invention is useful for control of ticks of the genus Ixodes, including *I. scapularis, I. pacificus, I spinipalpis, Dermacentor variabilis* and *D. andersoni*. The present invention is effective in arresting the transmission of an infective agent such as *Borrelia burgdorferi* from the treated rodent to another mammal such as a deer, mouse, chipmunk or human. In a preferred embodiment the treated rodent is a mouse (e.g., *Peromyscus* spp.) especially the white-footed mouse, *P. leocopus*, rat (e.g., *Rattus* spp. or *Neotoma* spp.), chipmunk (e.g., *Tamias* spp.), vole (e.g., *Microtus* spp.) or squirrel (e.g., *Sciurus* spp., *Tamiasciurus* spp. or *Spermophilus* spp).

Ectoparasiticides are known to those of ordinary skill in the art and are commercially available. A preferred ectoparasiticide according to the present invention is a compound of formula (I):

wherein:

$R_1$ is cyano, acetyl, $C(S)NH_2$, alkyl, haloalkyl, $C(=NOH)NH_2$ or $C(=NNH_2)NH_2$;

Or $R_1$ is a radical $R_2$ is $S(O)_n R_3$;

$R_3$ is alkyl or haloalkyl;

$R_4$ is H, halo, or a radical selected from $-NR_5R_6$, $C(O)OR_7$, $-S(O)_m R_7$, alkyl, haloalkyl, $-OR_8$, or $-N=C(R_9)(R_{10})$;

$R_5$ and $R_6$ are independently H, alkyl, haloalkyl, $-C(O)$ alkyl, or $-S(O)_r CF_3$; or $R_5$ and $R_6$ form together a divalent radical which may be interrupted by one or more heteroatoms;

$R_7$ is alkyl or haloalkyl;

$R_8$ is H, alkyl, or haloalkyl;

$R_9$ is H or alkyl;

$R_{10}$ is phenyl or heteroaryl, optionally substituted with one or more functional groups selected from hydroxy, halo, $-O$-alkyl, $-S$-alkyl, cyano, alkyl or combinations thereof;

X is N or the radical $C-R_{12}$;

$R_{11}$ and $R_{12}$ are, independently, H or halo.

$R_{13}$ is halo, haloalkyl, haloalkoxy, $-S(O)_q CF_3$ or $-SF_5$;

$R_{14}$ and $R_{15}$ are independently hydrogen, alkyl or haloalkyl;

$R_{16}$ is hydrogen, alkyl, haloalkyl, acyl, or alkoxycarbonyl;

A is $-O-$ or $-NR_{17}$ wherein $R_{17}$ is hydrogen, alkyl, haloalkyl, acyl or alkoxycarbonyl; and m, n, q, r are independently 0, 1 or 2.

The alkyl and alkoxy groups of the formula (I) are preferably lower alkyl and alkoxy groups, that is, radicals having one to four carbon atoms. The haloalkyl and haloalkoxy groups likewise preferably have one to four carbon atoms. The haloalkyl and haloalkoxy groups can bear one or more halogen atoms; preferred groups of this type include —$CF_3$ and —$OCF_3$.

Preferably, the 1-arylpyrazole has the following substitution: $R_1$ is CN; and/or $R_4$ is —$NR_5R_6$; and/or $R_5$ and $R_6$ are independently H, alkyl, haloalkyl, —C(O)alkyl, or —C(O)$OR_7$; and/or X is C—$R_{12}$; and/or $R_{13}$ is halo, haloalkyl, haloalkoxy, or —$SF_5$.

The most preferred 1-compound is 5-amino-3-cyano-1-(2,6-dichloro-4-trifluoromethylphenyl)-4-trifluoromethylsulfinylpyrazole (Fipronil).

The compounds of formula (I) can be prepared using techniques known to those of skill in the art, including for example, processes disclosed in International Patent Publications No. WO 87/03781, WO 93/06089 and WO 94/21606, WO 97/28126; WO 99/62903 as well as in European Patent Publication numbers 0295117, 0403300, 0385809, and 0679650, German Patent Publication 19511269 and U.S. Pat. Nos. 5,232,940 and 5,236,938, the disclosures of which are incorporated herein by reference.

The composition comprising the ectoparasiticide may further comprise inactive ingredients such as carriers, diluents, solvents, cosolvents and crystallization inhibitors. The ectoparasiticide is present in an amount effective to reduce larvae, nymphs or ticks on a small rodent upon topical application. Preferably, the ectoparasiticide, especially the compound of formula (I), is present in the composition at a concentration of from 0.1% to 5%, and preferably from 0.25% to 1%, and most preferably from 0.4% to 0.9% (weight/weight).

The composition is preferably substantially hydrophobic. Further, the composition is long-lasting such that it can be transferred to rodents with maintenance of ectoparasiticidal activity for up to three months, preferably six to eight months after placement at the locus, and more preferably for up to ten months, and most preferably for up to twelve months after placement at the locus.

In a preferred embodiment, the composition comprises a compound of formula (I), a crystallization inhibitor, an organic solvent, and an organic cosolvent. The composition is preferably hydrophobic. The crystallization inhibitor is preferably present at a concentration of 1 to 20% (w/v), and more preferably 5 to 15% (w/v).

A crystallization inhibitor prevents crystallization of the compound of formula (I) from the composition on the applicator or the hair or skin of the rodent. A crystallization inhibitor is defined by a test in which 0.3 ml of a solution containing 10% (w/v) of a compound of formula (I) in a solvent as defined hereinbelow and 10% of the putative inhibitor is placed on a glass slide at 20° C. for 24 hours. The presence of less than 10 crystals, a preferably few or no crystals, by observation with the naked eye after 24 hours is indicative of an inhibitor as defined herein.

Examples of crystallization inhibitors which can be used in the invention include polyvinylpyrrolidone, polyvinyl alcohols, copolymers of vinyl acetate and vinylpyrrolidone, polyethylene glycols, benzyl alcohol, mannitol, glycerol, sorbitol, polyethoxylated sorbitan esters; lecithin, carboxymethylcellulose sodium, acrylic derivatives such as methacrylate and others;

anionic surfactants such as alkali metal stearates, especially of sodium, of potassium or of ammonium; calcium stearate; triethanolamine stearate, sodium abietate; cetylsulphates, especially sodium laurylsulphate and sodium cetylsulphate; sodium dodecylbenzenesulphonate, sodium dioctylsulphosuccinate; fatty acids, especially those derived from copra oil;

cationic surfactants such as water-soluble quaternary ammonium salts of formula N⁺R'R"R'''R''''Y' in which the radicals R', R", R''', and R'''' are, independent of one another, optionally hydroxylated hydrocarbon radicals, and Y' is an anion of a strong acid, such as halide, sulphate and sulphonate anions; including in particular cetyltrimethylammonium bromide;

the amine salts of formula N⁺R'R"R''' in which the radicals R', R", and R''' are, independent of one another, optionally hydroxylated hydrocarbon radicals; including in particular octadecylamine hydrochloride;

non-ionic surfactants such as optionally polyethoxylated sorbitan esters, in particular Polysorbate 80, polyethoxylated alkyl ethers; polyethylene glycol stearate, polyethoxylated castor oil derivatives, polyglycerol esters, polyethoxylated fatty alcohols, polyethoxylated fatty acids, copolymers of ethylene oxide and propylene oxide; and amphoteric surfactants such as substituted lauryl betaine compounds, or preferably a mixture of at least two of these.

Most preferably, a crystallization inhibitor pair will be used, namely the combination of a surface-active agent and a filmogenic agent. Preferred filmogenic agents include different grades of polyvinylpyrrolidone, polyvinyl alcohol, and copolymers of vinyl acetate and vinylpyrrolidone. Preferred surface active agents include non-ionic surfactants, preferably polyethoxylated esters of sorbitan and especially the different grades of polysorbates, for example Polysorbate 80. The filmogenic agent and surface-active agent may be incorporated in close or identical quantities the total of which is within the preferred concentration range for the crystallization inhibitor as described above.

The organic solvent preferably has a dielectric constant of from 10 to 35, preferably from 20 and 30. The content of this organic solvent in the total composition preferably represents the remainder to 100% of the composition.

The organic cosolvent preferably has a boiling point lower than 100° C., preferably lower than 80° C., and a dielectric constant of from 10 to 40, preferably of from 20 to 30. The cosolvent is preferably present in the composition according to a weight/weight (w/w) ratio of co-solvent/solvent of from 1/15 to 1/2. The cosolvent is volatile in order to promote drying and is miscible with water and/or with the solvent. Although not preferred, the composition can optionally comprise water, especially at a rate from 0 to 30% volume/volume (v/v), preferably from 0 to 5%. The composition according to the invention may also comprise an antioxidant agent intended to inhibit oxidation in the air, this agent especially being present at a rate of from 0.005 to 1% (W/V), preferably from 0.01 to 0.05%.

Examples of organic solvents according to the invention include acetone, acetonitrile, benzyl alcohol, butyl diglycol, dimethyl acetamide, dimethyl formamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, especially N-methyl-pyrrolidone, diethylene glycol monoethyl ether, ethylene glycol, diethyl phthalate, or a mixture of at least two of these.

Suitable cosolvents for use in the present compositions include alcohols, such as absolute ethanol, isopropanol, and methanol. As antioxidant agent, conventional agents are especially used, such as butylhydroxyanisole, butylhydroxytoluene, ascorbic acid, sodium metabisulphite, propyl gallate, sodium thiosulphate, or a mixture of at least two of these.

Oils may advantageously be utilized in the compositions of the invention. For example, heavy oils such as mineral or vegetable including corn, soybean and peanut oil, and petroleum fractions such as paraffinic or aromatic hydrocarbons may be used.

The compositions according to the invention are generally prepared by simple mixing of the constituents as defined above.

Commercially available formulations of fipronil including FRONTLINE® from Merial, Inc and ADONIS® from Aventis CropScience S.A., Lyon, France, are suitable for use as the composition of the present invention.

The method of the invention provides to the rodent a dose of ectoparasiticide which is substantially harmless to the rodent. Preferably the amount of active ingredient applied to the rodent is from 0.001 mg to about 1 mg per application within the bait, preferably from 0.01 mg to 0.05 mg. The method of the invention also provides a small dose per application such that if an individual rodent visits the locus multiple times, the rodent is not harmed.

Such a dose must be able to protect the rodent itself for a period of at least one month, preferably from 1 to 3 months, and more preferably from 1 to 9 months. It is also provided according to the present invention that the rodents are not repelled from the enclosure so that they may be redosed by re-entering the enclosure. There may be an attractant associated with the enclosure which is highly attractive to the rodents in order to quickly dose many rodents within a predetermined area. A foodstuff may be associated with the enclosure. Most preferably, there is no poison for the rodent.

As a matter of an appropriate, safe method of providing such an enclosure to rodents in the loci which they are inhabiting or expected to inhabit, which loci are generally near humans, it is highly preferred that the ectoparasiticide composition in use be substantially inaccessible to the human hand. That is the ordinary user of such an enclosure would not be able to reach in or on the enclosure and be dosed with the ectoparasiticide.

Generally, the enclosure is placed at a transition zone which zone defines an interface between a woodland and a property where humans dwell. The enclosures are spaced one from another from 10 to 50 feet, preferably from 20 to 40 feet. Generally the enclosures are placed at the perimeter of the property. If the property is itself a woodland per se, there may be a grid of enclosures laid out to dose rodents within the property. The interface may be a verge.

Generally, there are from 1 to 50 enclosures placed per hectare within a defined area to be treated, preferably from 2 to 40, and more preferably from 10 to 35 enclosures per hectare.

In a park or other public facility, enclosures may be spaced along trails where humans may pass. Generally in such a setting, enclosures may be placed on one or both sides of a trail.

Preferably the enclosures may be placed and replaced on a periodic basis. In such a way, the method of the present invention provides a barrier to arthropods which may carry diseases. Each time the enclosures are replaced or replenished with the ectoparasiticide, the barrier is rejuvenated. The enclosures may be replaced or replenished from once per year to three times per year, depending on the population of rodents in the barrier locus.

In a particularly desirable aspect of the invention, there is provided a method of interrupting a disease cycle caused by arthropods of small rodents which method comprises treating a defined area by providing one or more enclosures of appropriate size to such rodents, the enclosures having one or more peripheral openings allowing entry and egress of rodents, the enclosure including at least one applicator arranged to contact a rodent; providing a composition comprising an ectoparasiticide on the applicator; and placing one or more enclosures in a locus where the rodents are expected, wherein the applicator is arranged and the composition is provided to apply an effective amount of the composition to the skin or hair of the rodent upon contact with the applicator.

In this aspect of the invention there is not a general expunging of the arthropod population away from the defined area, but rather a reduction in the infectious agent in that defined area.

The enclosure generally contains from 0.001 g to 1 g of active ingredient per device preferably from 0.01 g to 1 g of active ingredient, most preferably from 0.05 g to 0.150 g per device.

In general, in a highly preferred embodiment, the amount of compound of formula (I) used per hectare is from 0.1 g/ha to 3 g/ha per 6 months of use. More preferably, the amount of the compound of formula (I) is from 0.2 to 2 g per hectare per 6 months. In this way, the method of according to the invention may substantially reduce the number of rodents with the parasite per predetermined land area.

In a preferred embodiment, the enclosure has at least one peripheral opening to allow entry and egress of rodents and an applicator provided with an ectoparasiticide composition. More preferably, the enclosure further defines a passageway through which a rodent is attracted to proceed. As rodents are generally curious and seek out small spaces in which to lodge themselves or burrow or find food, this is a highly advantageous way in which to dose the rodents.

In the enclosure, the applicator is generally disposed in the path of the rodent, that is in the passageway. The applicator may be a small mop head, brush, wick, adsorbent panel or strip attached to the top of the enclosure or may be an insert lodged in a cavity in an interior wall which defines the passageway. In one preferred embodiment, the applicator is arranged to contact the anterior portion of a rodent that has entered the enclosure. The enclosure may include a bait located therein and the passageway is preferably arranged between the opening and the bait. The applicator may be rechargeable or replaceable, preferably from outside the enclosure and without opening the enclosure. The composition may be applied to the applicator in a manner suitable to the particular applicator, for example, by soaking or dipping the applicator in the composition, or painting, spraying, squirting or otherwise applying the composition to the applicator.

The enclosure preferably includes a lower member and an upper member which are hinged together to form a boxlike enclosure that can be swung open and closed. The members are preferably made of plastic, such as injection molded plastic. A suitable enclosure is available from Bell Laboratories of Madison, Wis. and sold under the product name "Protecta Jr. Bait Station". This enclosure is 6"×5½" and 3" high, and has a durable hinge connecting the upper member and the lower member and includes a screw lock to secure the enclosure in a closed condition so that children or larger animals are not able to open the enclosure and reach the contents thereof.

In a preferred embodiment, the applicator comprising a flexible material is attached to the upper member with a portion thereof hanging into the enclosure such that when a rodent enters and moves through the chamber, the fibrous strands of the applicator rub across the fur or skin of the rodent and apply a small amount of the composition thereon to the skin or fur of the rodent. The flexible material may be strands a fibrous material, such as strands of cotton wick.

Figure 10:
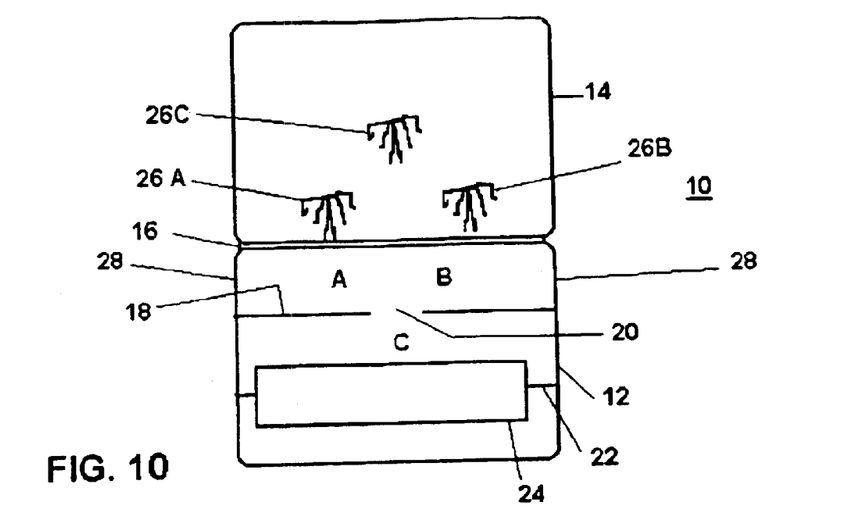
FIG. 10 is a top view showing an open apparatus according to the present invention with the top fully open.
Figure 11:
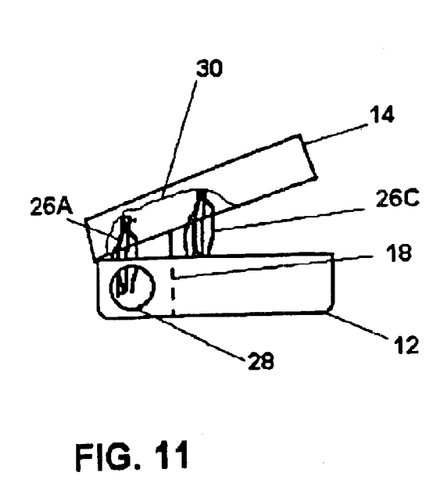
FIG. 11 is a side view of the FIG. 10 apparatus showing the arrangement with the top in a nearly closed condition.

A preferred enclosure according to the present invention is depicted in FIGS. 10 and 11. Referring to FIG. 10, enclosure 10 of the present invention is shown in a fully opened condition. The enclosure includes a lower member 12 and an upper member 14 which are hinged together at 16 to form a boxlike enclosure that can be swung open and closed. Members 12 and 14 are preferably made of plastic, such as injection molded plastic. The enclosure has a durable hinge 16 connecting the upper member 14 and the lower member 12 and includes a screw lock to secure the enclosure in a closed condition so that children or larger animals are not able to open the enclosure and reach the contents thereof.

Lower member 12 includes sidewall openings 28 which are visible in the side view of FIG. 11 and which are arranged in an appropriate size to permit the entry of a rodent such as a mouse. Inside member 12 there is provided an interior wall 18 which separates the chamber into an entry passageway having openings 28 and an inner bait chamber in which there is provided a bait 24. Bait 24 is preferably a solid bait mounted on a steel horizontal rod 22 which keeps the bait off any moisture on the floor of the enclosure. Interior wall 18 has an opening 20 by which a rodent may enter the inner bait chamber. The top cover member 14 is provided with 3 chemical applicators 26A, 26B and 26C. Applicators 26 each comprise a collection of fiber strands, such as strands of cotton wick, which are attached by one end to top cover member 14. Applicators 26A, 26B and 26C are arranged on cover 14 at positions such that the strands of each applicator will hang in regions A, B and C respectively of enclosure 10 when cover 14 is in the closed position. Accordingly, when a rodent enters the chamber and moves through regions A, B, or C, the fibrous strands of the applicator rub across the fur or skin of the rodent and apply a small amount of the chemical thereon to the skin or fur of the rodent. In the embodiment shown in FIGS. 10 and 11 the applicators are arranged in positions where a rodent is likely to pass when exploring the inside of the enclosure. In particular, the rodent will be entering by one of openings 28 and be attracted to bait 24 in the inner bait chamber of the enclosure. In reaching the bait 24 the rodent is likely to pass through and contact with either applicator 26A or 26B in the passageway from opening 28 to opening 20 and thereafter also engage applicator 26C while passing through opening 20 and approaching bait 24.

It will be understood by those familiar with the art that different size, shape and configuration of enclosures may be used in accordance with the invention and that the particular location of applicators 26 in such enclosures may be at different locations according to the arrangement of passages in the enclosures. It will also be understood by those skilled in the art that instead of having fibrous strands hanging from the interior top wall of top of enclosure 10, one might provide different arrangements for application of chemicals to a rodent passing through the chamber. For example, bristles may be used projecting from the top, bottom or side walls of passages through which a rodent passes and thereby contacting the skin or fur of the animal. Alternatively these may be arranged a soft fibrous mass, such as cotton or foam rubber over which the rodent must crawl.

Figure 12:
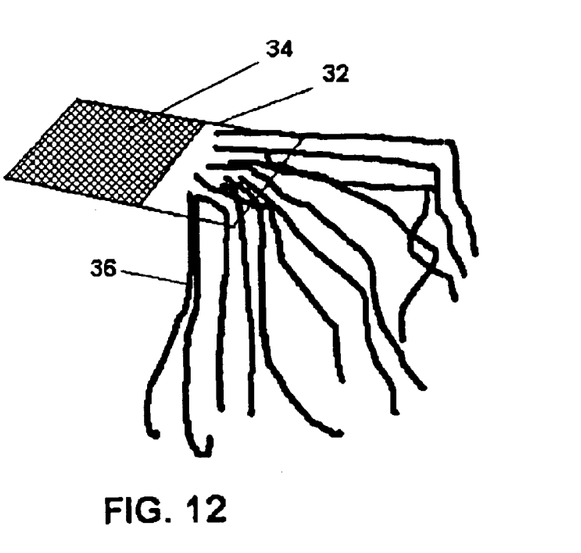
FIG. 12 is a detailed perspective view of an applicator useful in the apparatus of FIGS. 10 and 11.

It should be additionally recognized that it may be advantageous to provide applicators 26 in a configuration which can be easily replaced with new applicators to provide a renewed supply of chemicals. Accordingly, the applicators may be formed as shown in FIG. 12 wherein strands 36 of fiber are glued or otherwise affixed to a piece of tape 32 having an adhesive portion 34 which can adhere to the inside of top member 14 at positions such as those shown in FIG. 10. Alternatively a hook and loop fastener, such as Velcro® can be used. In this manner applicators 26A, 26B and 26C may easily be replaced after several weeks of use by an attendant to provide new applicators with a new supply of chemicals. The old applicators may discarded and new applicator attached to the top 14 of enclosure 10 by affixing with the adhesive or the hook and loop fastener.

While there has been described what is believed to be the preferred embodiment of this present invention, those skilled in the art will recognize that other and further changes and modifications may be made thereto without departing from the spirit of the present invention, and it is intended to claim all such changes and modifications as fall within the true scope of the invention.

The following nonlimiting examples serve to further illustrate the present invention.

EXAMPLE 1

Figure 1:
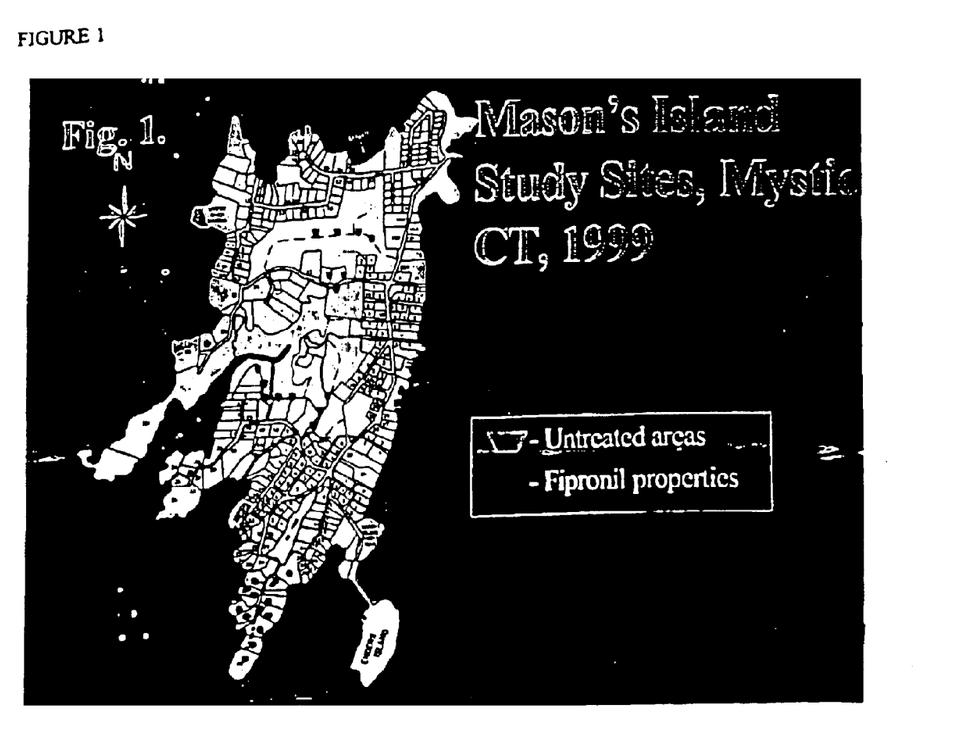
FIG. 1 is a map of Mason's Island depicting sites treated by the method of the present invention.

A field trial was conducted from April to September, 1999 on Mason's Island, Mystic, Conn. FIG. 1 shows that the fipronil treatment area consisted of 13 contiguous residences with a total area of 9.88 acres (about 4 hectares). Four sites situated in undeveloped natural areas were used as untreated controls.

Figure 2:
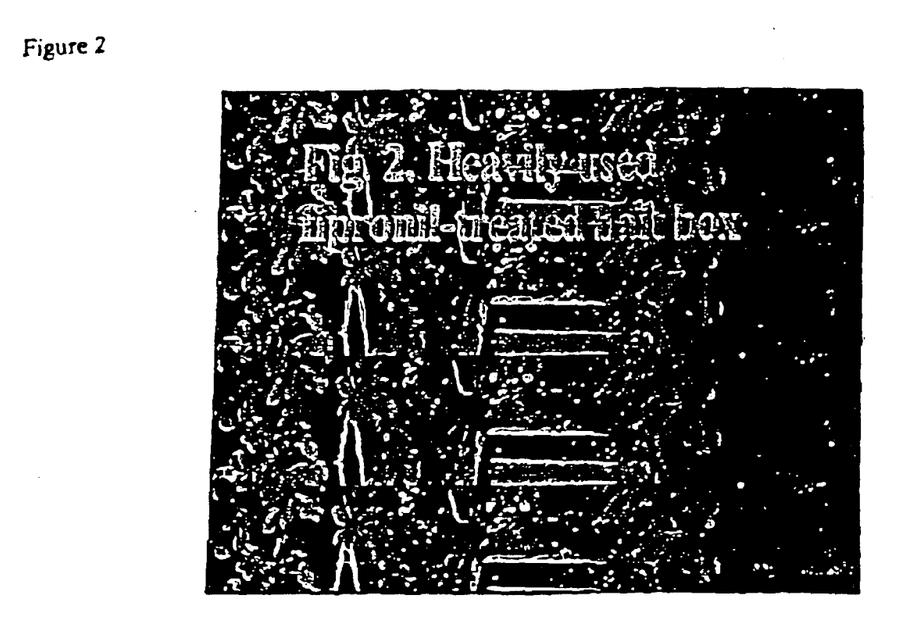
FIG. 2 depicts a mouse bait box modified to contain applicators onto which an ectoparasiticidal composition is applied.

Modified Protecta Jr. (Bell Laboratories, Madison, Wis.) mouse bait boxes (FIG. 2) were used in this study. The modifications were as follows: a cotton yarn wick was stapled to the underside of the lid just in front of the feeding area entry; two adsorbent nylon strips were affixed to the outer edges of the food block trays. Two Detex monitoring blocks (Bell Laboratories, Madison, Wis.) were placed in each box, 2–3 ml of fipronil topical formulation was applied to the wick and adsorbent strips with a squirt bottle, and the lid was closed and locked with a set screw prior to placement on properties. A 0.43% w/w formulation of fipronil was used in May and June and this was replaced by a 1% w/w formulation from July through September.

White-footed mice were live-trapped using 3"×3"×10" Sherman mouse traps (Sherman Trap Co., Tallahassee, Fla.). Pre-treatment trapping was conducted in April and May and post-treatment trapping from June through September to determine: 1) distribution of mice on individual properties, 2) tick burdens on animals, and 3) spirochete infection rates in mice between treated and untreated plots. Each mouse was anesthetized, ectoparasites were removed, ear tissue was collected for spirochete culture, mice were then bled, weighed, measured, ear-tagged and released at the point of capture. In July and August cloth drags were used to collect host-seeking larval ticks for comparison with results of host-associated tick data.

Based upon pre-treatment mouse distribution and abundance data, a total of 125 bait boxes were set out on 13 residences. Boxes were spaced approximately 30 feet apart along the interface with maintained landscaping and wood lot or scrub brush. The number of boxes/property ranged from 4 to 20, depending on property size and presence of suitable mouse habitat. Initial treatment with fipronil began on May 17 and at approximate 4-week intervals each box was re-baited with 2 food blocks and the wick and strips were replenished with 2–3 ml of fipronil formulation. A record of relative use by white-footed mice was kept for each box during the trial.

Fipronil Bioassay: To better determine the most efficacious concentration of fipronil active ingredient for use in the bait box method of tick control, a trial was conducted using treated and untreated laboratory mice challenged with nymphal *Ixodes scapularis*. Individual groups of 5 mice were treated with 20 microliters (one drop) of 1%, 0.75%, 0.5% and 0.43% of fipronil topical oil formulation micropipetted between the scapulae. Five mice were used as untreated controls. Individual mice were challenged with 10 nymphs each on days 14, 28 and 42. During tick challenge mice were held over water in a triple barrier/cage system. Ticks that fed to repletion were collected from the water and used as a measurement for acaricidal activity.

Figure 3:
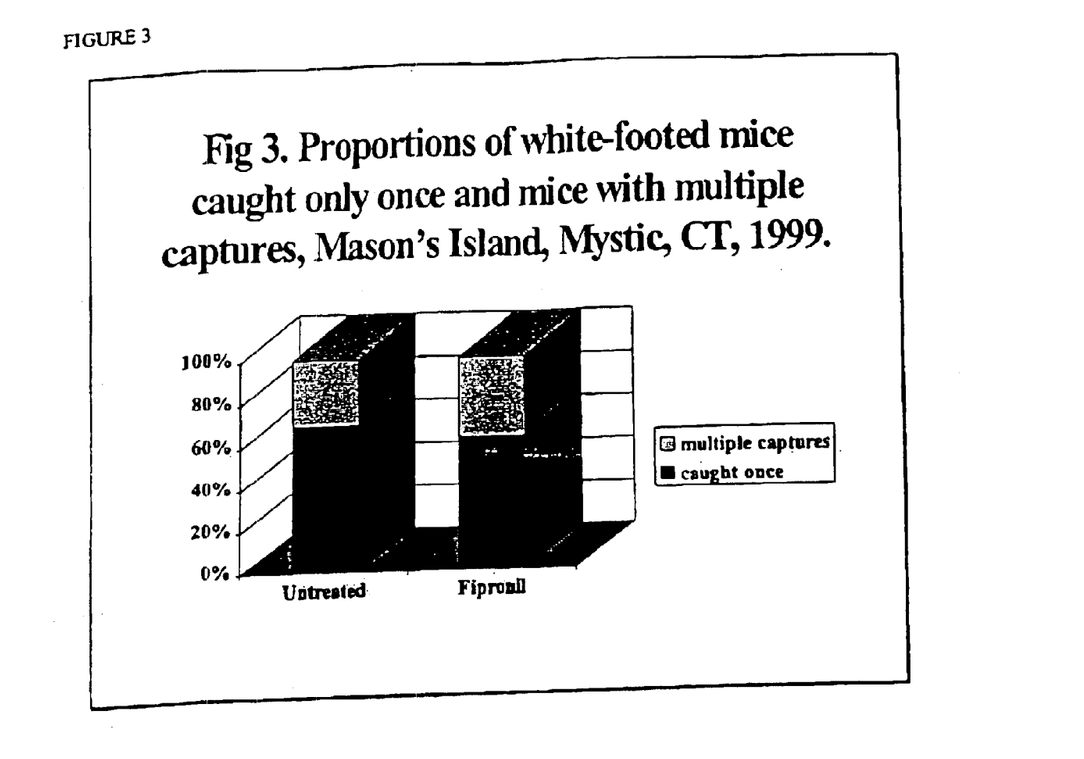
FIG. 3 is a graph depicting mice caught once and mice caught multiple times in a field trial.

Results: Table 1 shows that a total of 2,223 trap nights resulted in 425 captures representing 313 individual *Peromyscus leucopus*, the principal reservoir for *Borrelia burgdorferi*. A total of 1,608 ticks were collected from these mice. An interesting observation was the proportion of mice captured only once and those with multiple captures. In both the treated and untreated areas, 70% of the mice were captured only once and apparently moved out of the study area (FIG. 3). This indicates the necessity for an acaricide that has residual activity and requires a small quantity to protect mice from tick infestation with just one or a few exposures to the AI.

TABLE 1

Peromyscus leucopus collected on
Mason's Island April–September 1999 (2,223 Trap nights)

| Untreated Area | 208 Captures | 149 mice |
| Fipronil Designate Area | 217 Captures | 164 mice |
| Total | 425 Captures | 313 mice |

Figure 4:
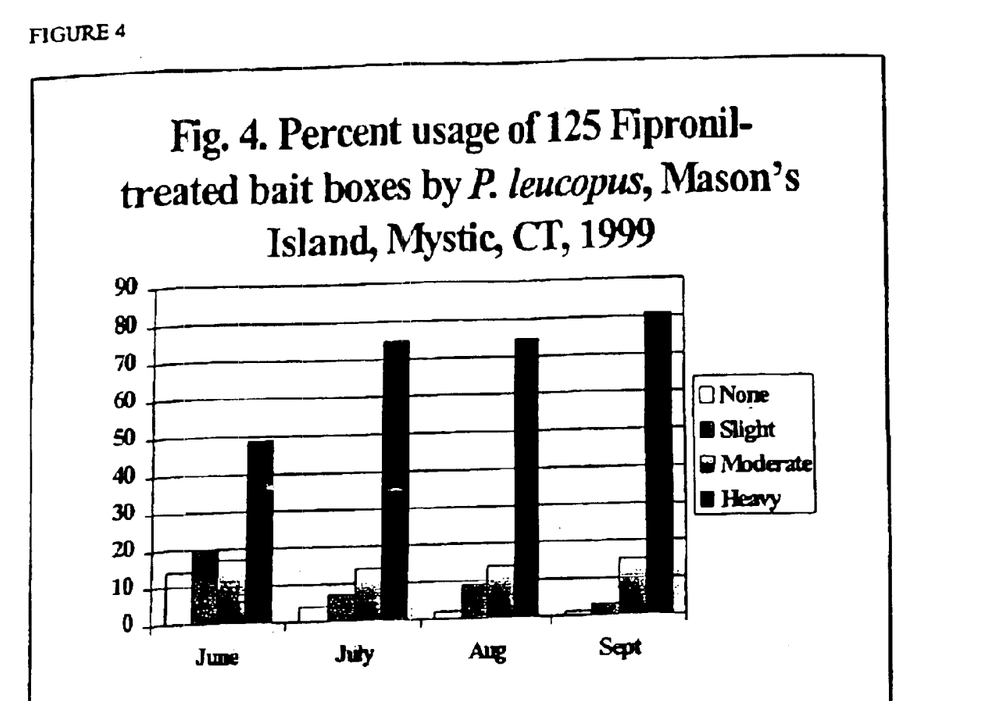
FIG. 4 is a graph depicting relative use of the enclosures of the invention by month.

1) Relative use of bait boxes by mice—The relative acceptance and use of these devices by *P. leucopus* was ≧85% in June and increased to >95%from July through September (FIG. 4). A total of 0.5 liter of 0.43% Adonis® (Aventis CropScience S.A., Lyon, France) and 0.9 liter of 1% Adonis® were used to treat bait boxes during this study. This volume translates to a total of 11.15 grams (0.39 oz.) of fipronil on 13 properties (9.88 acres).

Figure 5:
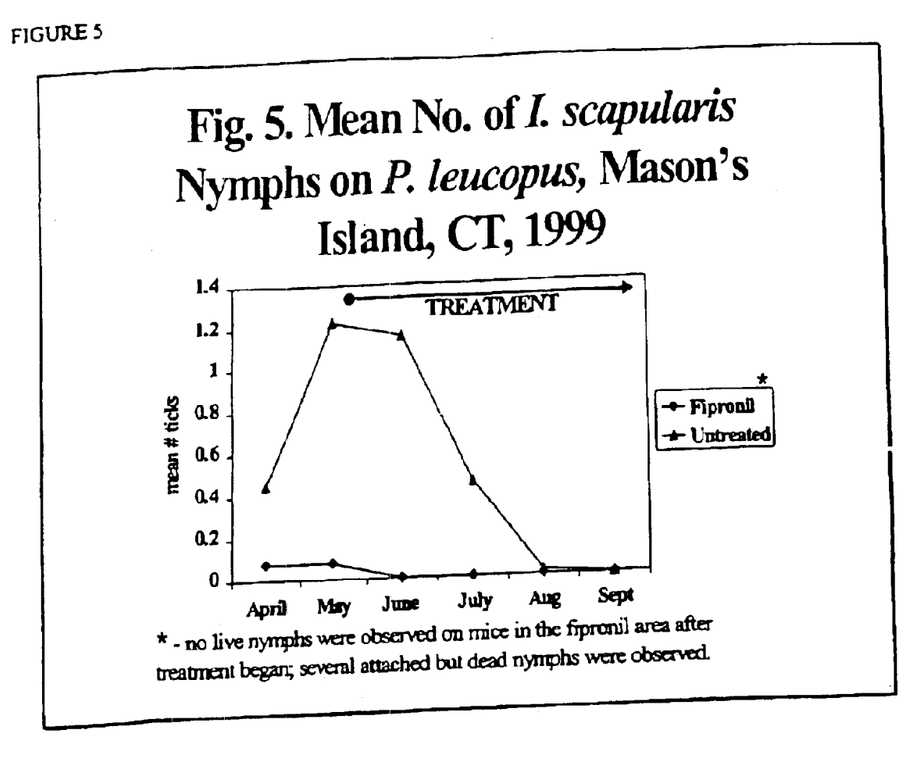
FIG. 5 is a graph comparing the number of nymphs per mouse in treated versus untreated plots.

2) Reduction of ticks on treated mice—During the two pretreatment collection periods, the mean number of *I. scapularis* nymphs/white-footed mouse was much lower in the designated fipronil study area as compared to the natural area (FIG. 5). The fipronil study area is situated on the southern tip of Mason's Island and is more exposed to high wind and subject to colder temperatures than the more protected center of the island where the control areas are located. Weather conditions during the weeks prior to and during collection in April and May were very rainy, windy and cold and may have been responsible for inhibiting normal host-seeking activity patterns for nymphs on the highly exposed and windswept island tip. Nevertheless, live nymphs were not found on mice after fipronil treatment; whereas, nymphs were present on mice in the untreated area through August. It was observed during June and July that several mice in the fipronil-treated area had nymphs attached to the head area, but these ticks had died in situ before feeding. Dead ticks attached to mice in the untreated area were not observed.

Figure 6:
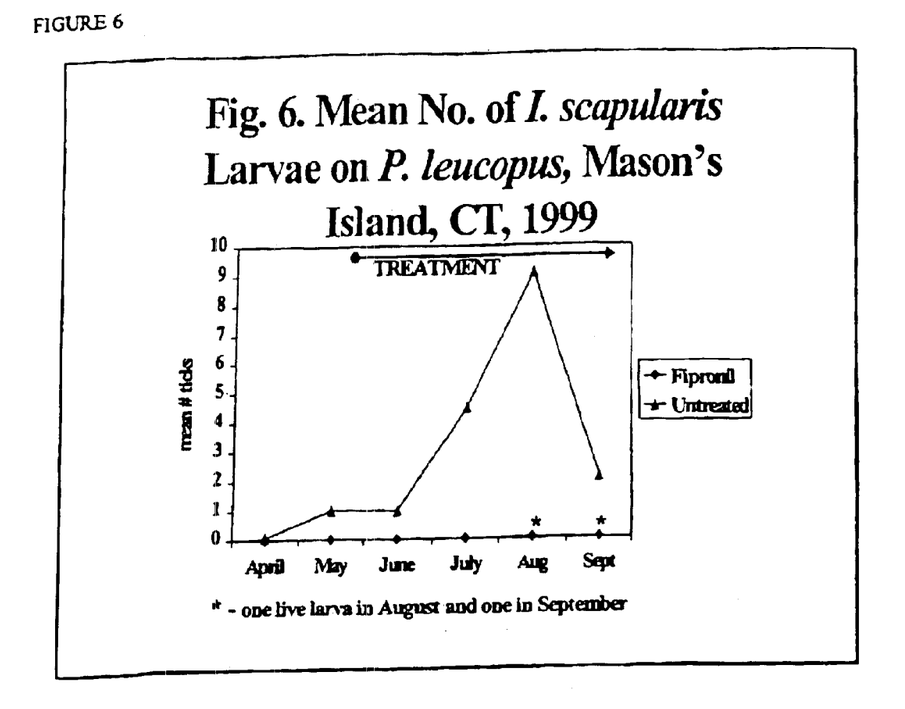
FIG. 6 is a graph comparing the number of larvae per mouse in treated versus untreated plots.
Figure 7:
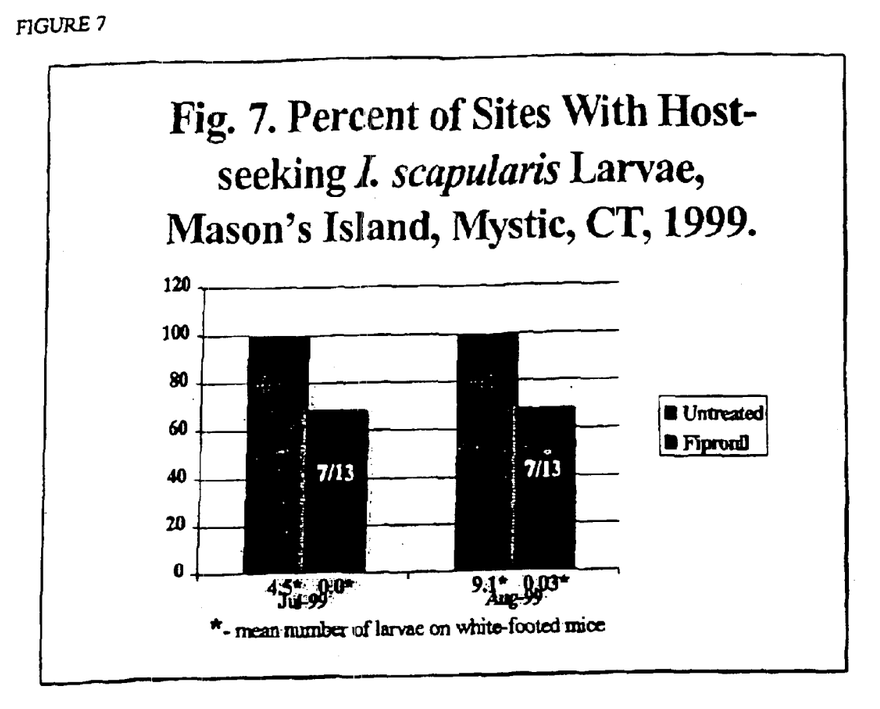
FIG. 7 is a graph depicting the percent of sites with larvae in treated and untreated areas.

The reduction of *I. scapularis* larvae on mice by fipronil was dramatic when compared to the untreated plots. FIG. 6 shows that larvae on untreated mice were abundant from June through September. Larvae on treated mice were not present during the course of the study except for one engorged larva on a mouse in August and one larva on a mouse in September (FIG. 6). In order to further determine the status of the larval tick population in our study areas, larvae were sampled by cloth drags on each of the treated properties and untreated sites. Results of this endeavor are presented in FIG. 7. Host-seeking larvae were abundant in all the untreated areas during July and August with corresponding mean number of larvae/mouse at 4.5 and 9.1, respectively. In contrast, host-seeking larvae were not found on six of the smallest properties in the fipronil area, but were present in numbers similar to untreated areas on the other seven (54%) of the treated properties. The mean number of larvae/mouse in the treated area during July and August was 0 and 0.03, respectively. Fipronil significantly reduced the number of larvae feeding on mice on treated properties.

3) Impact of fipronil on the natural transmission cycle of *B. burgdorferi*—Individual captured mice were tested for infection with *B. burgdorferi* by culture of ear biopsy tissue in BSK H growth media. Table 2 shows that the natural transmission cycle of Lyme disease on Mason's Island is very intense.

TABLE 2

Prevalence and Distribution of *Borrelia burgdorferi* Infection
Among *Peromyscus leucopus*, Mason's Island, Mystic, CT 1999

| Treatment Areas | No. of P. leucopus captures | No. of P. leucopus | % of spirochete-infected mice | % of properties with infected mice |
| --- | --- | --- | --- | --- |
| Untreated Control | 208 | 149 | 69% | 100% |
| Fipronil Area | 217 | 164 | 38% | 92% |
| Totals | 553 | 428 | 50% | 96% |

Figure 8:
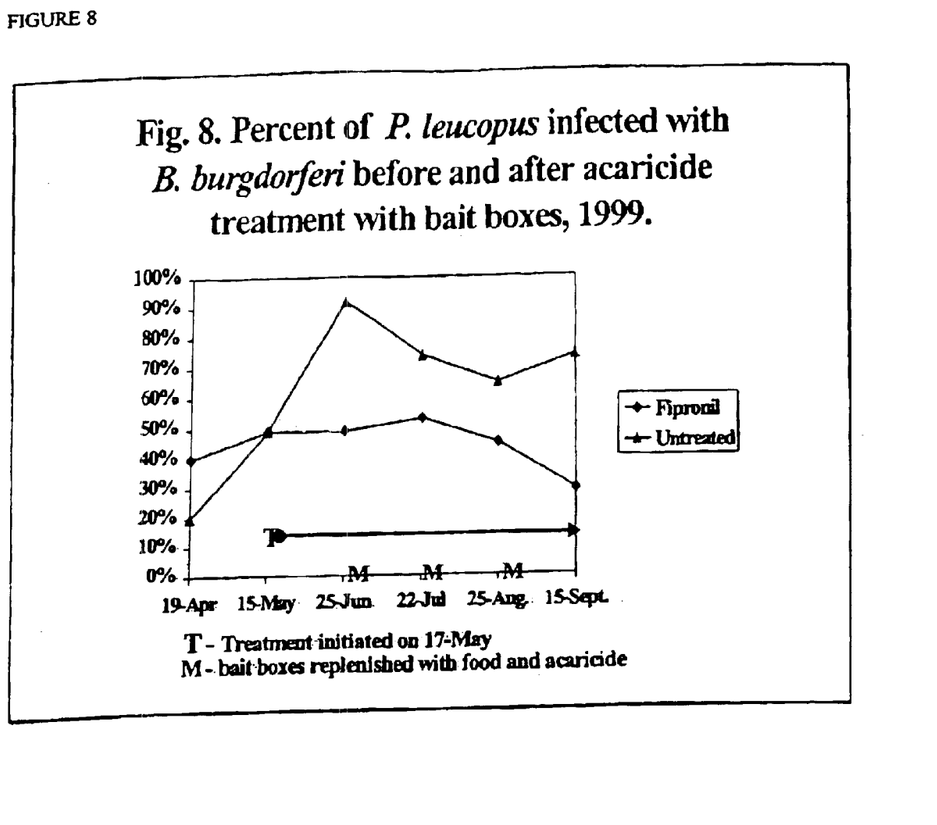
FIG. 8 is graph depicting the monthly incidence of spirochete infection in treated versus untreated areas.

*B. burgdorferi*-infected *P. leucopus* (69% of 149 mice) were present at all untreated control sites. In comparison, fewer mice (38%) were infected in the fipronil-treated area even though 12/13 (92%) of the properties had infected mice distributed on them. The differences in prevalence of *B. burgdorferi* infection among treated and untreated mice was due to the acaricidal activity of fipronil. FIG. 8 shows the monthly incidence of spirochete infection among white-footed mice as it relates to fipronil treatment. In the untreated areas the incidence of infected mice began at 20% in April and by June, the peak of nymphal activity, the incidence rose above 90% and remained above 60% throughout the ensuing summer months. In the fipronil-treated area the incidence of infection in April was 40%. The infection rate in May was 50% which was equivalent to the untreated area (FIG. 8). Following the placement of fipronil-treated bait boxes on May 17, the infection rates did not significantly increase as compared to the untreated controls. In fact, a steady decline in incidence of spirochete-infected mice was recorded in August and September. To further study the effect of fipronil on the incidence of *B. burgdorferi* infection, we reviewed rates of infection among naive young of the year (body mass <17 g) and naive adult mice (body mass >17 g).

Figure 9:
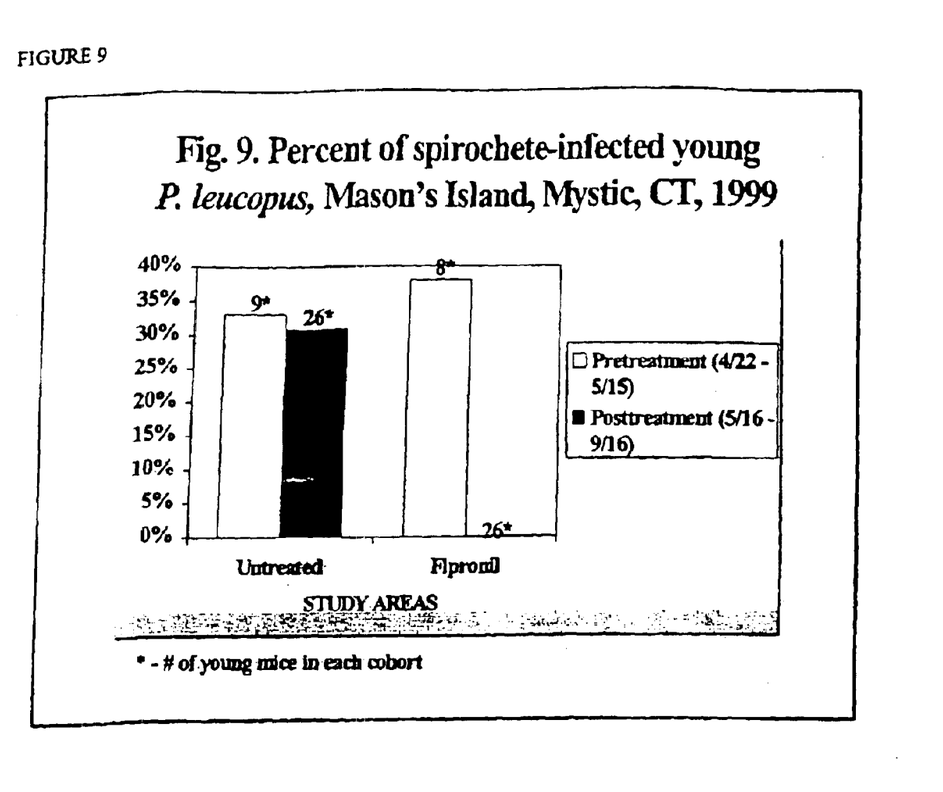
FIG. 9 is a graph comparing the incidence of spirochete infection in young mice between treated and untreated areas.

FIG. 9 compares the incidence of spirochete infection in young mice between treated and untreated areas. During the pretreatment period in April and May, similar numbers of young mice were captured in both areas with similar rates of infection. However, dramatic differences were apparent for the post-treatment period, i.e., in the untreated area 30% of 26 young mice became infected; whereas, in the fipronil area none of 26 young became infected. Likewise, a significant number of spirochete-naive adult mice were protected from infection by *B. burgdorferi* (Table 3) after fipronil-treated bait boxes were set out on properties.

TABLE 3

Spirochete Infections in Recaptured Adult White-footed Mice following Fipronil Treatment, Mason's Island, Mystic, CT 1999

|  | No. of mice + at first capture, remained + | No. of mice – at first capture, became + | No. of mice – at first capture, remained – |
|---|---|---|---|
| Untreated Area | 25 | 13 | 4 |
| Fipronil Area | 18 | 4 | 14 |

Chi-square test: p-value = 0.01, significant difference between populations

4) Fipronil bioassay—A total of 25 mice and 750 nymphal *I. scapularis* were used in this laboratory trial. The volume of 20 microliters (one average-sized drop) was considered the smallest amount of liquid acaricide that a mouse would apply to itself on a single visit to a bait box. Table 4 shows that the concentration of 0.75% (=150 micrograms) is the optimum amount of fipronil to kill ticks on mice for 30 days after a single exposure to a treated bait box.

TABLE 4

Bioassay of Adonis: Least M of 20 µl of Fipronil Required to Kill *I. scapularis* Nymphs* on Treated Mice (single application)

| | % OF NYMPHS FED TO REPLETION | | |
|---|---|---|---|
| TEST GROUPS* | 14 DAYS | 28 DAYS | 42 DAYS |
| CONTROLS | 72% | 76% | 73% |
| 1.00% (200 µg/mouse) | 0% | 0% | 2% |
| 0.75% (150 µg/mouse) | 0% | 2% | 6% |
| 0.50% (100 µg/mouse) | 0% | 8% | 24% |
| 0.43% (85 µg/mouse) | 0% | 16% | 30% |

*5 mice challenged with 10 nymphs/group; a total of 25 mice and 750 ticks tested Conclusions: This example indicates that fipronil-treated bait boxes are highly effective in killing immature deer ticks on white-footed mice. The high acaricidal activity of fipronil dramatically reduced the number of *B. burgdorferi*-infected mice on treated properties. The fact that significantly few larval ticks successfully fed on mice in the treated area will result in dramatic reduction of risk for residents being exposed to infected nymphs on their properties. Adverse environmental impact of fipronil and this delivery strategy is extremely minimal. Only 11.15 grams (0.39 oz) of fipronil active ingredient were applied on a total area of 9.88 acres during this trial. About 2 ml of liquid each per 125 bait boxes remained on the wicks at the end of the study. Deducting that volume, it is estimated that the total amount of fipronil actually applied to mice over 6 months on 13 properties encompassing 9.88 acres (4 hectares was 8.65 grams (about 2.1 g/ha). This material and delivery system provides a safe, effective tool for controlling tick-borne diseases.

EXAMPLE 2

A field trial testing fipronil (FRONT LINE TOP SPOT®) on native rodent-associated ticks was conducted in a Rocky Mountains foothills habitat in Larimer County, Colo. Treated and untreated plots consisted of 35 rat dens within 5 hectares each. A mark-release-capture study with *Neotoma mexicana* began in April, and captured rats were anesthetized and ticks removed, identified and quantified. The principal tick on *N. mexicana* is *I. spinipalpis*, a nidicolous, competent vector in enzootic transmission cycles in Colorado, California and Oregon. Pretreatment tick infestation rates (>76%) and abundance (>5.35/rat) were comparable in both treated and untreated plots. Fipronil was passively applied to rats as they entered and exited modified commercially available bait boxes as described in Example 1. Treated bait boxes were set out in May, left in place, and retreated and rebaited at four-week intervals through August. Collections were made at 1, 4, 8, 12 and 16 weeks post-application. *N. mexicana* collected in the untreated control area numbered 92 with 150 total captures resulting in 1273 fleas and ticks. In the fipronil area, 110 individual rats were collected with a total of 179 captures resulting in 416 fleas and ticks. Comparison of tick burdens (number of ticks per treated rat/number of ticks per untreated rat) resulted in *I. spinipalpis* control levels as follows: week 1, 25%; week 4, 90%: week 8, 75%; week 12, 97%: and week 16: 93%. This study indicates that fipronil applied to rodents using modified manufactured bait boxes is a useful method for long-term control of Ixodes ticks.

We claim:

1. A method of controlling ectoparasites of small rodents comprising providing one or more enclosures of appropriate size to said rodents, said enclosures having one or more peripheral openings allowing entry and egress of rodents therein, each of said enclousures comprising at least one applicator arranged to contact rodents that enter said enclosure; providing a composition consisting essentially of an ectoparasiticide and inactive ingredients on said applicator; and placing said one or more enclosures in a locus at which said rodents are expected; said applicator being arranged and said composition being provided to apply an ectoparasiticidally effective amount of the composition to the skin or hair of said rodents upon contact with said applicator, wherein said applicator is inaccessible to contact with a human hand from said one or more peripheral openings and further wherein said ectoparasiticide is fipronil which is present in said composition in an amount of from 0.1% to 5% by weight and present in said one or more enclosures in an amount of from 0.001 gram to 2.0 grams per enclosure.

2. The method of claim 1 wherein the ectoparasites are arthropods.

3. The method of claim 1 wherein the rodent is a mouse, rat, vole, chipmunk or squirrel.

4. The method according to claim 2 wherein the ectoparasites are ticks of the genus Ixodes.

5. The method according to claim 1 wherein the applicator is a brush.

6. The method according to claim 1 wherein the ectoparasiticide is present in said composition in an amount of from 0.25% to 1% by weight.

7. The method according to claim 1 wherein the composition is hydrophobic.

8. The method according to claim 1 wherein the applicator is a small mop head.

9. The method of claim 1 wherein the amount of ectoparasiticide is from 0.100 g per enclosure to 2.0 g per enclosure.

10. The method according to claim 1 wherein the percent by weight of the ectoparasiticide in the composition is from 0.4% to 0.9%.

11. The method according to claim 1 wherein the one or more enclosures further comprise a foodstuff for the rodent.

12. The method according to claim 1 wherein from one to ten enclosures are placed per hectare of locus.

13. The method according to claim 12 wherein each enclosure further defines a passageway through which a rodent is attracted to proceed.

14. The method according to claim 13 wherein the applicator is disposed in the passageway.

15. The method according to claim 1 wherein the applicator is disposed adjacent to or near one of the one or more peripheral openings.

16. The method according to claim 1 wherein the applicator is rechargeable from the outside of the enclosure without necessity to open the enclosure.

17. The method according to claim 1 wherein the applicator is replaceable.

18. A method for preventing the transmission of diseases by arthropod vectors comprising providing one or more enclosures of appropriate size for small rodents, said enclosures having one or more peripheral openings allowing entry and egress of rodents therein, said enclosure including at least one applicator arranged to contact rodents that enter said enclosure; providing a composition consisting essentially of fipronil and inactive ingredients on said applicator; and placing said one or more enclosures in a locus at which said rodents are expected; said applicator being arranged and said composition being provided to apply an ectoparasiticidally effective amount of fipronil to the skin or hair of said rodents upon contact with said applicator, wherein said applicator is inaccessible to contact with a human hand from said one or more peripheral openings, further wherein said fipronil is present in said composition in an amount of from 0.1% to 5% by weight and present in said one or more enclosures in an amount of from 0.001 gram to 2.0 grams per enclosure.

19. The method according to claim 18, wherein the percent by weight of the fipronil in the composition is from 0.25% to 1%.

20. A method of controlling ectoparasites of small rodents comprising providing one or more enclosures of appropriate size to said rodents, said enclosures having one or more peripheral openings allowing entry and egress of rodents therein, each of said enclosures comprising at least one applicator arranged to contact rodents that enter said enclosure; providing a composition consisting essentially of an ectoparasiticide and inactive ingredients on said applicator; and placing said one or more enclosures at a transition zone between a woodland and a property where humans dwell; said applicator being arranged and said composition being provided to apply an ectoparasiticidally effective amount of the composition to the skin or hair of said rodents upon contact with said applicator, wherein said applicator is inaccessible to contact with a human hand from said one or more peripheral openings and further wherein said ectoparasiticide is fipronil which is present in said composition in an amount of from 0.1% to 5% by weight and present in said one or more enclosures in an amount of from 0.001 gram to 2.0 grams per enclosure.

21. The method according to claim 20, wherein two or more of said enclosures are used and the enclosures are spaced apart from one another at a distance of from 10 to 50 feet.

22. The method according to claim 20, wherein two or more of said enclosures are used and the enclosures are spaced apart from one another at a distance of from 20 to 40 feet.

23. The method according to claim 20, wherein said transition zone contains from 1 to 50 enclosures per hectare.

24. The method according to claim 20, wherein said enclosures are replaced, or the ectoparasiticide within said enclosures is replenished, from once to three times per year.

25. A method of controlling ectoparasites of small rodents comprising providing one or more enclosures of appropriate size to said rodents, said enclosures having one or more peripheral openings allowing entry and egress of rodents therein, each of said enclosures comprising at least one applicator arranged to contact rodents that enter said enclosure; providing a composition consisting essentially of an ectoparasiticide and inactive ingredients on said applicator; and placing said one or more enclosures in an area to be treated; said applicator being arranged and said composition being provided to apply an ectoparasiticidally effective amount of the composition to the skin or hair of said rodents upon contact with said applicator, wherein said applicator is inaccessible to contact with a human hand from said one or more peripheral openings and further wherein said ectoparasiticide is fipronil which is present in said composition in an amount of from 0.1% to 5% by weight, said fipronil being present in said one or more enclosures in an amount of from 0.001 gram to 2.0 grams per enclosure.

26. The method according to claim 25, wherein two or more of said enclosures are used and the enclosures are spaced apart from one another at a distance of from 10 to 50 feet.

27. The method according to claim 25, wherein two or more of said enclosures are used and the enclosures are spaced apart from one another at a distance of from 20 to 40 feet.

28. The method according to claim 25, wherein said area to be treated contains from 1 to 50 enclosures per hectare.

29. The method according to claim 25, wherein said enclosures are replaced, or the ectoparasiticide within said enclosures is replenished, from once to three times per year.

30. The method according to claim 25, wherein said area to be treated contains from 2 to 40 enclosures per hectare.

31. The method according to claim 25, wherein said area to be treated contains from 10 to 35 enclosures per hectare.

* * * * *